(12) United States Patent
Cadio et al.

(10) Patent No.: US 12,138,088 B2
(45) Date of Patent: Nov. 12, 2024

(54) DISPOSAL SYSTEM

(71) Applicant: Roche Diabetes Care, Inc., Indianapolis, IN (US)

(72) Inventors: Michel Alain Jean Marie Cadio, Carmel, IN (US); Ernest Graeme Harvey, Avon, IN (US); Justin David Adams, Noblesville, IN (US); Vijay Thambiah, Mason, OH (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 88 days.

(21) Appl. No.: 17/842,252

(22) Filed: Jun. 16, 2022

(65) Prior Publication Data

US 2022/0304763 A1    Sep. 29, 2022

Related U.S. Application Data

(63) Continuation of application No. PCT/US2020/065800, filed on Dec. 18, 2020.
(Continued)

(51) Int. Cl.
*A61B 50/36* (2016.01)
(52) U.S. Cl.
CPC .................. *A61B 50/36* (2016.02)
(58) Field of Classification Search
CPC .............. A61B 50/36; A61B 5/150022; A61B 2050/3006; A61B 5/150267; A61B 5/150305; A61B 5/150358
(Continued)

(56) References Cited

U.S. PATENT DOCUMENTS 4,228,758 A * 10/1980 Dornau .................. B63B 59/02
                                                        215/385
4,898,309 A *  2/1990 Fischer ................ A47G 25/904
                                                        248/314
(Continued)

FOREIGN PATENT DOCUMENTS

WO    2010096054 A1    8/2010
WO    2013070664 A1    5/2013

OTHER PUBLICATIONS

International Search Report and Written Opinion; PCT/US2020/065800; Apr. 19, 2021; pp. 1-10.

*Primary Examiner* — Steven A. Reynolds
*Assistant Examiner* — Prince Pal

(57) ABSTRACT

This disclosure is directed to a disposal container system enabling storage of used or contaminated articles having a generally flat, strip-shaped configuration, such as diagnostic biosensors. The disposal container is removably mountable to a supply container, and has an insertion portion provided in a wall of the disposal container. The insertion portion has a contour configured externally to guide deposit of a flat, strip-shaped article through a narrow slit, the contour further configured internally to deflect any loose articles in the interior space of the disposal container away from any accidental alignment with the slit which would cause free extraction of the articles. The disposal container may be configured for engagement with a supply container, such as a round or non-round vial, in a bottom-cap configuration or in a side-by-side configuration, by way of an engagement portion.

15 Claims, 10 Drawing Sheets

Related U.S. Application Data

(60) Provisional application No. 62/953,258, filed on Dec. 24, 2019.

(58) Field of Classification Search
USPC ........ 206/366, 438, 363, 365, 364; 220/908; D24/224, 130
See application file for complete search history.

(56) References Cited

U.S. PATENT DOCUMENTS

| | | | | |
|---|---|---|---|---|
| 4,917,243 A * | 4/1990 | Abrams | ............... | A61M 5/3216 220/908 |
| D311,876 S * | 11/1990 | Kiegami | ....................... | D24/232 |
| 5,084,028 A * | 1/1992 | Kennedy | ............. | A61M 5/3213 221/281 |
| 5,240,108 A * | 8/1993 | Tonna | ................... | A61B 50/362 211/84 |
| 5,245,117 A * | 9/1993 | Withers | ................. | A61M 5/002 405/129.55 |
| 5,323,901 A * | 6/1994 | Outlaw, III | ........... | A61B 50/362 206/370 |
| 5,368,580 A * | 11/1994 | Suzuki | ................ | A61M 5/3216 604/263 |
| D411,014 S * | 6/1999 | Berger | ........................ | D24/223 |
| 6,135,305 A * | 10/2000 | Brady | ................. | A24F 19/0078 220/366.1 |
| 6,530,479 B2 * | 3/2003 | Hernandez | ............. | A61M 5/008 206/370 |
| D519,209 S * | 4/2006 | Bublewitz | .................... | D24/176 |
| 7,513,363 B2 * | 4/2009 | Brown | ................ | A61M 5/3205 312/211 |
| 7,600,638 B2 * | 10/2009 | Finnestad | .............. | A61B 50/36 206/370 |
| 7,815,046 B2 * | 10/2010 | Sansoucy | ............ | A61B 50/3001 221/102 |
| 8,157,159 B2 * | 4/2012 | Al-Hadhoud | ......... | B65F 1/1607 220/264 |
| 8,201,704 B2 * | 6/2012 | Finnestad | ............... | B65F 1/163 220/23.91 |
| 8,434,616 B2 * | 5/2013 | Erickson | ................ | A61M 5/002 220/908 |
| 8,560,460 B2 * | 10/2013 | Mallett | ................. | B07C 5/3412 705/308 |
| 8,672,124 B2 * | 3/2014 | Burgess | ................. | B65D 85/04 206/363 |
| 8,922,367 B2 * | 12/2014 | Denny | .................... | G16H 20/13 604/59 |
| 8,950,578 B2 * | 2/2015 | Erickson | .......... | A61B 5/150022 206/370 |
| 9,745,101 B2 * | 8/2017 | Freedman | ............. | B65D 43/162 |
| 9,914,126 B2 * | 3/2018 | Chan | ....................... | B01L 99/00 |
| 10,252,008 B2 * | 4/2019 | Erickson | .............. | A61B 50/362 |
| 10,722,427 B2 * | 7/2020 | Cantor | .................... | A61J 1/165 |
| 2003/0132129 A1 * | 7/2003 | Erickson | .......... | A61M 5/3205 206/366 |
| 2003/0226879 A1 * | 12/2003 | Auclair | ................... | B65D 5/721 229/122 |
| 2004/0020814 A1 * | 2/2004 | Mousset | ................ | A61B 50/31 206/438 |
| 2004/0173488 A1 * | 9/2004 | Griffin | ................... | A61B 50/36 206/363 |
| 2005/0103662 A1 * | 5/2005 | Iske | ......................... | A61B 50/10 206/363 |
| 2006/0243634 A1 * | 11/2006 | Brown | ................ | A61M 5/3205 206/571 |
| 2006/0278545 A1 * | 12/2006 | Henning | ................ | A61B 5/157 206/363 |
| 2007/0029213 A1 * | 2/2007 | Hall | .................... | B65D 83/0454 206/217 |
| 2007/0119738 A1 * | 5/2007 | Clegg | ................... | A61M 5/008 206/363 |
| 2007/0196242 A1 * | 8/2007 | Boozer | .................. | A61B 50/30 422/400 |
| 2008/0173658 A1 * | 7/2008 | Ronning | .............. | B65D 25/005 220/661 |
| 2008/0308441 A1 * | 12/2008 | Erickson | .......... | A61B 5/150717 206/438 |
| 2009/0032423 A1 * | 2/2009 | Japuntich | ............... | A61B 42/40 220/23.83 |
| 2011/0259471 A1 * | 10/2011 | Maness | .................. | A61B 50/37 141/69 |
| 2017/0043346 A1 * | 2/2017 | Welch | .................... | B65D 25/24 |
| 2017/0108486 A1 * | 4/2017 | Joseph | .................. | B65D 53/02 |
| 2018/0141713 A1 * | 5/2018 | Drossman | ............. | B65D 25/02 |
| 2023/0087144 A1 * | 3/2023 | Goradesky | ................ | A24F 1/26 |

* cited by examiner

DISPOSAL SYSTEM

PRIORITY CLAIM

The present application is a bypass Continuation application claiming the priority benefit of International Application No. PCT/US2020/065800 filed Dec. 18, 2020, the disclosure of which is incorporated herein by reference in its entirety, and which claims the benefit of the priority filing of U.S. Provisional Patent Application No. 62/953,258, filed Dec. 24, 2019, the disclosure of which is incorporated herein by reference in its entirety.

TECHNICAL FIELD OF THE INVENTION

The present application relates to a unique disposal system, namely containers for small, flat, strip-shaped articles, particularly to auxiliary containers which are mountable or otherwise removably connectable to a vial configured to contain small, flat, strip-shaped articles, and more particularly to disposal containers for used or contaminated biosensors having a generally flat configuration, which containers are removably mountable to a vial containing unused biosensors, and which may further be configured for easy deposit of such biosensors and for restricted removal of biosensors from the interior of the disposal container once deposited.

BACKGROUND

The present invention generally relates to a unique container for receiving and storing used or contaminated biosensors within the container. More specifically, but not exclusively, the present invention concerns a unique container that can be sized and configured for mounting to a distinct container such as a vial.

People who analyze their bodily fluid, such as blood or interstitial fluid, for any number of characteristics, such as triglycerides, ketones, or more likely blood glucose levels for diabetics, must dispose of the used testing devices, such as biosensors. Disposal devices have been developed to store both used lancets (used. e.g., for pricking the person's skin for obtaining a sample of bodily fluid) and/or used biosensors. Lancets or biosensors may be said to be "used" after having been exposed to bodily fluid. Such disposal devices must have an opening configured to receive various shapes to accommodate for disposal of both lancets and biosensors. However, it would be useful to have a container specifically configured for the unique challenge of receiving and retaining small, flat-shaped articles such as biosensors.

Patients who test their own blood glucose levels often encounter the situation in which they must safely dispose of their used biosensor in a hygienic way. In a public setting, these patients often cannot find a disposal device in which used biosensors will be disposed in a sanitary manner. Often these patients must carry their used biosensors with them until the patient can dispose of them in a sanitary manner. Typically, in a private setting, such as a home of a patient, a patient must expend time and energy to find the proper disposal device in their home in which the used biosensors can be sanitarily disposed and contained within. Patients faced with these obstacles typically skip testing their blood glucose levels at the required time interval thereby risking an increased likelihood of an inappropriate blood glucose level, and even death, or they dispose of the devices in an inappropriate manner or in a manner in which used biosensors may be found lying freely around, such as on countertops, in furniture, on the floor, in testing kit packs, or in other items such as drawers or shoes. Indeed, many patients complain that used biosensors can often be found 'everywhere' as a reminder of an incurable chronic illness.

Another potential difficulty with a biosensor disposal container is that typically the container is provided separate from and in addition to the testing devices, such as a blood glucose meter, and supply containers, such as a vial of biosensors, already required by the user. These additional items detract from the discretion for their disease that many diabetics prefer, and the person must spend time and energy searching for the separate devices and containers as well as keep track of them all.

Another obstacle often associated with a biosensor is safe and hygienic disposal of a used biosensor. For example, the user or medical practitioner using the biosensor would not want to accidentally touch another person or themselves with a contaminated biosensor, thereby potentially exposing this person or themselves to disease.

Another area for improvement of biosensor disposal practices is that separate self-contained and disposable (i.e. single-use) disposal containers may add to the volume of discarded articles for trash or landfill collection. Once a single-use disposal container has no further capacity for receiving used biosensors, typically the entire container is then disposed, wherein the container itself typically has an external profile that defines a greater volume than the aggregated volume of biosensors contained in it. Having a container that retains biosensors while in use but can be emptied for further use not only saves waste from the container itself but also reduces the resources that would otherwise be required for manufacture of single-use containers that are always discarded when filled.

Additional problems that have been identified which may be solved by the present invention include (i) patients with diabetes typically carry around an additional container or bag, which stores used test strips that would be considered bio-hazardous material; (ii) some patients simply discard used test strips in standard trash receptacles, store them in pockets, purses, or other convenient places until a later time upon which proper disposal is available; (iii) current disposal systems are cumbersome to carry or prone to expose unused test elements to the risk of contamination or damage from excessive exposure to air, light, or moisture; (iv) current disposal systems are typically not reusable and not easy to sanitize; and (v) the constant reminder of used test strips in and around personal articles can be an additional burden to the psychological wellness of patients with diabetes.

Thus, there remains a need for further improvement in this field.

SUMMARY

These objects and others that will be appreciated by a person of ordinary skill in the art have been achieved according to the embodiments of the present invention disclosed herein. Among the solutions provided by the present invention are (i) a detachable, isolated compartment and opening to minimize risk of contamination or compromise (e.g. biological fluid, oxidation, humidity, etc.) of unused test elements when disposing of used test elements; (ii) keeping used test strips separate from unused test strips, minimizing the risk of accidental strip reuse; (iii) a design that supports proper disposal of bio-hazardous blood glucose test strips and may also be easily emptied, sanitized, and re-used; (iv) an aid to psychological wellness of people with diabetes by keeping used test strips out of sight for easy and proper disposal; (v) a snap-on vial strip disposal container with a "V" slot design which provides users a convenient storage system that allows for contaminated (used) blood glucose test strips (biosensors) to be inserted into the container easily with no concern associated with strips falling out of the storage container until time of disposal; and (vi) effortless "snap on, snap-off" industrial design which ensures that the used blood glucose test strips can be disposed at a time that is convenient and appropriate for the user.

In one embodiment, the present invention comprises a disposal container removably mountable to a supply container, having a used-biosensor insertion portion provided in a wall of the container with an external contour configured to guide deposit of a biosensor through a narrow slit, and an internal contour configured to deflect any loose biosensors from any accidental alignment with the slit which would cause free extraction of the biosensor.

In a further embodiment, the present invention relates to a container for receiving a plurality of flat, strip-shaped articles (e.g. blood glucose biosensors) which have been used or otherwise contaminated. In one aspect, the container includes a generally planar base having a periphery, a sidewall extending upwardly from the periphery of the base to a top opening, the base and sidewall defining an interior space having a receptacle portion and an engagement portion. The receptacle portion is located proximal to the base and configured for receiving and retaining a plurality of flat strip-shaped articles, such as blood glucose biosensors. The engagement portion is located distally to the base and is configured to detachably receive and retain a lower portion of a vial via a fitted engagement proximate to the top opening. In another aspect, the engagement portion engages the bottom of a biosensor supply vial in a bottom cap configuration, in a similar fashion as a pen and pen cap. The sidewall of the container has an insertion portion comprising a slit configured to receive a single flat strip-shaped article into the receptacle portion. In one aspect of this embodiment, the slit is oriented orthogonally to the base. The insertion portion further comprises a pair of generally planar and rigid opposing surfaces tapered inwardly from an exterior of the sidewall to the slit, the slit being generally defined in the area where the tapered opposing surfaces converge, such that the spacial arrangement of the slit is inset from the sidewall. The tapered opposing surfaces are generally configured to facilitate alignment of a flat strip-shaped article for insertion through the slit into the receptacle portion. The sidewall further comprises an interior surface, wherein the interior surface at the engagement portion is contoured corresponding to the exterior surface of a vial which is to be received therein. The interior surface further comprises at least one internally extending ledge located downwardly spaced from the top opening. The ledge is provided to delineate a transition from the engagement portion to the receptacle portion, and comprises a stop configured to prevent the portion of a supply vial received in the engagement portion from extending into the receptacle portion. The interior surface at the insertion portion is contoured in accordance with the inwardly tapered opposing surfaces to define an interior deflector configured to deflect any loose flat strip-shaped articles contained within the receptacle portion from accidental alignment with the slit which would cause free extraction of said article.

In one aspect of this embodiment, the fitted engagement proximate the top opening comprises a snap-fit system provided on the interior surface of the sidewall in the engagement portion.

In another aspect of this embodiment, the snap-fit system comprises a plurality of inwardly extending tabs on the interior surface of the sidewall in the engagement portion, the tabs being spaced apart downwardly from the top opening at or slightly above the ledge, and configured to frictionally engage a corresponding ridge provided on a lower portion of a vial inserted into the engagement portion.

In an alternative aspect of this embodiment, rather than a snap-fit system, the fitted engagement comprises a frictional retention arrangement wherein the top opening and an interior surface of the engagement portion are shaped according to the exterior dimensions of a lower portion of a vial to be inserted therein.

In yet another aspect of this embodiment, the slit has a generally vertical orientation and the insertion portion is located in the sidewall at a location spaced upwardly from the base.

In yet another aspect of this embodiment, the slit has a length and width dimensioned to just accommodate the length and width of a flat strip-shaped article intended for insertion therethrough.

In yet another aspect of this embodiment, the length and width dimensions of the slit are no more than 5% to 50% larger than the cross-sectional length and width of a flat strip-shaped article intended for insertion therethrough, whereby the likelihood of accidental alignment of a loose article within the receptacle portion is minimized.

In yet another aspect of this embodiment, the base has a non-round shape.

In yet another aspect of this embodiment, the base comprises a generally oval shape and the sidewall in coordination with the base comprises a generally oval-shaped cylinder having opposing first and second rounded short ends, the insertion portion being located in the sidewall at one of the first and second short ends.

In yet another aspect of this embodiment, the sidewall extends upwardly from the base non-vertically such that interior angle between the base and the sidewall at the first short end is between 0 and 30 degrees less than 90 degrees, and the interior angle between the base and the sidewall at the second short end is a corresponding amount of degrees more than 90 degrees relative to the interior angle at the first short end.

In aspects of this embodiment in which the ledge does not extend entirely within the interior space to completely divide the receptacle portion from the engagement portion, the container may engage a correspondingly shaped vial, wherein the vial provides the divider and closes the receptacle portion from the environment other than as provided by the slit in the insertion portion of the sidewall. In that way, the container, when a user desires to discard any articles contained in the receptacle portion, can be removed from the engagement with the vial and thus expose the receptacle portion, wherein any articles may be appropriately discarded through the top opening.

In yet a further embodiment, the present invention relates to a disposal container removably mountable to a supply container, having a used-biosensor insertion portion provided in a wall of the container with a contour configured externally to guide deposit of a biosensor through a narrow slit and configured internally to deflect any loose biosensors from any accidental alignment with the slit which would cause free extraction of the biosensor. The insertion portion further comprises a pair of generally planar and rigid opposing surfaces tapered inwardly from an exterior of the sidewall to the slit, the slit being generally defined in the area where the tapered opposing surfaces converge, such that the spacial arrangement of the slit is inset from the sidewall. The tapered opposing surfaces are generally configured to facilitate alignment of a flat strip-shaped article for insertion through the slit into the receptacle portion. The wall further comprises an interior surface. The interior surface at the insertion portion is contoured in accordance with the inwardly tapered opposing surfaces to define an interior deflector configured to deflect any loose flat strip-shaped articles contained within the receptacle portion from accidental alignment with the slit which would cause free extraction of said article.

In one aspect of such embodiment, the wall comprises an exterior surface portion configured for engagement with a vial. In one example of this aspect, the exterior surface portion includes a concave side configured to receive a portion of a sidewall of a corresponding vial. In another example, the vial comprises an upstanding cylindrical shape, and the exterior surface portion of the disposal container receives a portion of the cylindrical sidewall from about 10 degrees to about 180 degrees of the circumference of the vial.

In another aspect of such embodiment, the exterior surface portion of the disposal container comprises at least one pair of clip arms configured for deflectable frictional engagement with a vial In yet another aspect, the disposal container comprises a bottom platform extending from a base of the disposal container for supporting a vial or other supply container to which the disposal container is mounted.

In yet another aspect of such embodiment, the disposal container comprises a hatch having a living hinge securing the hatch to the disposal container, wherein any contents of the disposal container deposited therein through the narrow slit may be emptied from the disposal container by opening the hatch. The hatch is then returned to a closed position in order to close the receptacle portion of the disposal container from the environment, other than through the narrow slit, for further use in receiving more articles such as used biosensors.

In yet another aspect of such embodiment, the insertion portion is provided in a top wall of the disposal container.

In yet another aspect of such embodiment, the insertion portion provided in a top wall of the disposal container further comprises brackets for aligning the disposal container with the hinge of a lid provided on a supply container (e.g. flip top vial), wherein the container is maintained in a generally fixed position relative to the disposal container. In addition, by aligning the hinge of a flip top vial between brackets which flank the insertion portion in the top wall of the disposal container, the vial lid obstructs the use of the insertion portion, leading to the advantage that the insertion portion is isolated from unused biosensors that are provided in the vial, when the lid of the vial is in an open position.

In other embodiments, the disposal container may include means for seeing inside the receptacle portion. In one aspect, at least a portion of the upstanding wall or upwardly extending sidewall comprises a transparent or translucent window enabling visualization of the interior space of the receptacle portion. In another aspect, the wall or sidewall, at least about the receptacle portion, is comprised of a transparent or translucent material, such as a transparent plastic, so that the majority if not entirety, as desired, of the interior space of the receptacle portion can be seen by a user through the material. In such aspects of a window or use of a transparent or translucent material, a user is able to monitor the fill-level of the receptacle portion, and/determine when the receptacle portion of the container has reached a capacity that should be emptied for further use.

In yet other embodiments, the interior surface at the narrow slit of the insertion portion includes a protrusion that cooperates with the interior deflector formed by the contour of the interior surface at the insertion portion to further prevent accidental extraction of biosensors out of the container through the slit.

In yet other embodiments, at least a portion of the exterior surface of the disposal container is configured for enhanced gripping by a user. For example, in one aspect, the exterior surface may be formed integrally with portions providing surface features or contours that provide a tactile grip when handled by a user's fingertips. Alternatively, a separate material, such as non-slip rubber, may be added to at least a portion of the exterior surface, such as a plurality of raised 'dots' or similar surface features that provide a natural tactile grip for users. Such enhanced gripping is conducive to providing a user better handling of the disposal container when, e.g., attaching it to or detaching it from a corresponding supply vial.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
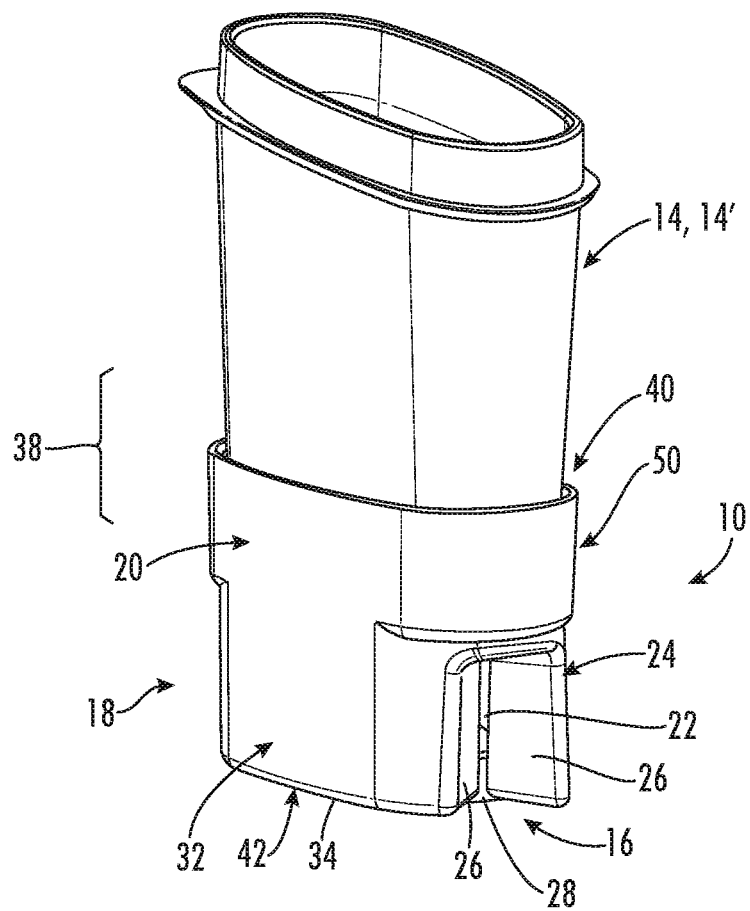
FIG. 1 shows a perspective view of an embodiment of a disposal container in a use-condition mounted as a bottom cap to a non-round vial.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail; although it will be apparent to those skilled in the relevant art that some features that are not relevant to the present invention may not be shown for the sake of clarity.

The present invention generally concerns a disposal container 10 for used or contaminated articles 12 having a generally flat, strip-shaped configuration, such as biological fluid sample biosensors like blood glucose test strips, wherein the container is releasably mountable to a vial 14 or other container supplying unused articles, and has a unique insertion portion 16 designed to facilitate insertion of the articles into a receptacle portion 18 of the container and prevent removal or extraction (accidental or purposeful) of the articles from the receptacle portion. As a general principle, the disposal container of the present invention is adaptable in its external profile configuration for use with a variety of different vials, without limiting the scope of the present invention except as may be expressly described herein in connection with specific embodiments or aspects of the embodiments which may be claimed.

In one embodiment, the present invention comprises a disposal container 10 removably mountable to a supply container 14, having a used-biosensor insertion portion 16 provided in a wall 20 of the container with a contour configured externally to guide deposit of a biosensor 12 through a narrow slit 22 and configured internally to deflect any loose biosensors 12' from any accidental alignment with the slit which would cause free extraction of the biosensor.

The insertion portion 16 of the present invention generally comprises the slit 22 and the contoured portion 24 of the wall 20 of the container 10. The insertion portion 16 exteriorly defines a pair of generally planar opposing surfaces 26 tapered inwardly in a 'V' configuration toward the slit 22 which is defined by the convergence 28 of the tapered surfaces 26. The tapered surfaces 26 generally serve to funnel flat, strip-shaped articles 12 toward and into alignment with the slit 22 for easy insertion through the slit. Interiorly, the wall 20 of the container at the insertion portion 16 defines a deflector 30 which serves to deflect loose articles 12' away from the slit 22, generally preventing articles from extraction back through the slit.

The position of the insertion portion 16 on the disposal container 10 may be determined according to the overall configuration of the container and the shape of the vial 14 or other supply container to which the disposal container may be mounted. In general, the location is selected to optimize the effectiveness of the deflector 30 to prevent any loose articles 12' from becoming perfectly aligned with the slit 22 in a way that allows such article to pass back through the slit and out of the container. In one embodiment, the insertion portion 16 is located on a sidewall 32 of the disposal container and in an orientation orthogonal to the bottom 34 of the container. In other embodiments, the insertion portion 16 is located on a sidewall 32 of the disposal container 10 and spaced upwardly from the bottom 34 of the container. In yet other embodiments, the insertion portion 16 is provided in a top wall 36 of the container 10, wherein the articles 12' generally settle at the bottom of the container and require the container to be shaken or otherwise turned upside down in order to even attempt to align a loose article 12' for extraction through the slit 22, but wherein the deflector 30 effectively deflects articles away from the slit. Other useful selections for the location of the insertion portion 16 in the container 10 may become apparent to those of skill in the art in view of the description of the present invention herein.

According to the embodiment shown in FIGS. 1-6, the disposal container 10 is configured to be releasably mounted to a non-round vial 14', and is mounted to such vial in a bottom cap configuration 38 wherein the container 10 may be snap-fit or friction-fit to the bottom 40 of the vial 14'. It will be appreciated that the external configuration of the container may, for ornamental purposes, be matched to the external configuration of the vial, such that the container may appear as merely an extension to the vial. Thus, for example, where an oval vial such as the vial used for holding ACCU-CHEK Guide test strips has a 'forward lean' as viewed from a side profile perspective (wherein the front wall of the vial defines an obtuse angle with the base of the vial whereas the rear wall of the vial defines an acute angle with the base of the vial), the disposal container in some embodiments of the present invention may similarly be configured with a complementary 'forward lean' as may be seen in FIG. 5, wherein the angle α of the bottom 34 and the front wall 66 is generally obtuse, whereas the angle β between the bottom 34 and the rear wall 67 is generally acute. In one aspect, angle α is greater than 90 degrees and no more than 120 degrees, and angle β is less than 90 degrees and more than 60 degrees. In other aspects, the angles α and β are generally equivalently greater than and less than, respectively, 90 degrees so as to configure the front 66 and rear 67 walls essentially parallel to each other.

The container 10 as shown comprises a generally planar base 42 having a periphery 44 and a sidewall 32 extending upwardly from the periphery to a top opening 46. The base 42 and the sidewall 32 define an interior space 48 comprising a receptacle portion 18, where loose articles 12' are retained after insertion into the container, and an engagement portion 50 configured to retainably receive a portion of the exterior of a corresponding vial. In this embodiment, the engagement portion 50 is configured to receive a portion of the bottom end 40 of a non-round vial 14' as shown in FIG. 1.

The receptacle portion 18 in this embodiment is located proximal to the base 42 and and is sized and configured for receiving and retaining a plurality of flat, strip-shaped articles 12 such as biosensors, and further such as blood glucose test strips. The engagement portion 50 is located distally to the base 42 and configured to detachably receive and retain a portion of a vial. The engagement is generally a fitted engagement in which a portion of the vial is received through the top opening 46. In one aspect, the fitted engagement comprises a snap-fit engagement, structural aspects of which are described further hereinbelow. In another aspect, the fitted engagement comprises a frictional engagement, such as engagement of a pen cap with either the writing-end or the bottom end of a pen.

Selectively located in the sidewall 32 adjacent the receptacle portion 18 is an insertion portion 16 comprising a slit 22 or other narrowed opening configured to receive a single flat, strip-shaped article 12 for passage from the external environment to the interior space 48 of the receptacle portion 18. The insertion portion 16 generally comprises a pair of generally planar opposing surfaces 26 tapered inwardly from an exterior 52 of the sidewall 32 to the slit 22. The slit 22 is generally defined at the convergence 28 of the opposing surfaces 26. In one aspect, the opposing surfaces 26 have a 'V' configuration in order to funnel and orient a flat, strip-shaped article 12 for passage through the slit 22 into the receptacle portion 18. As such, the configuration of opposing surfaces 26 facilitate alignment of the article 14 with the slit 22.

Figure 2:
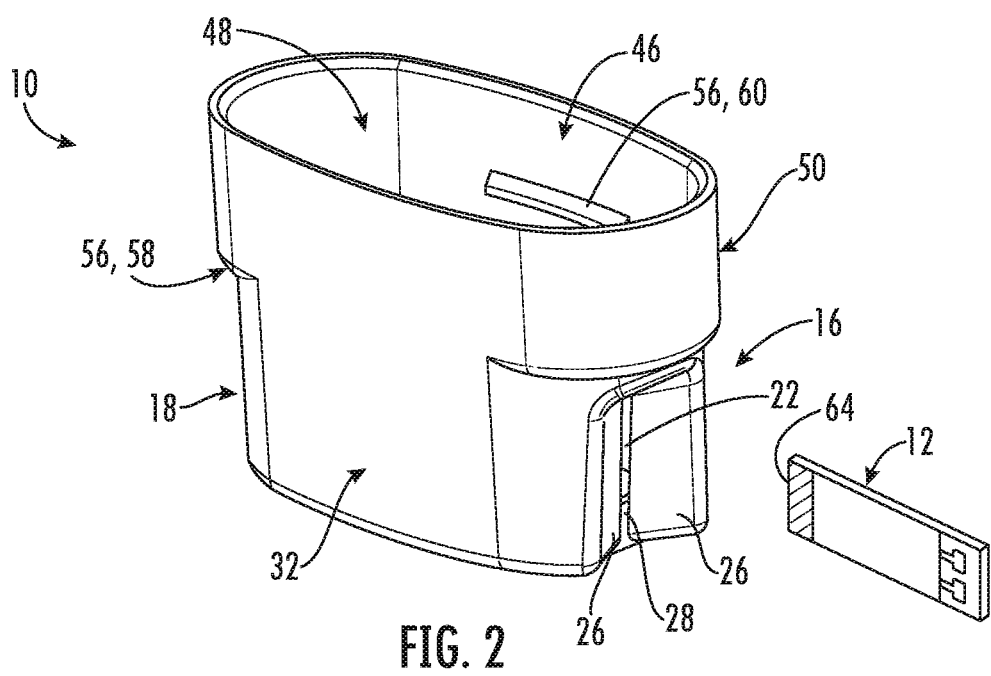
FIG. 2 shows a perspective view of the embodiment of the container of FIG. 1.
Figure 3:
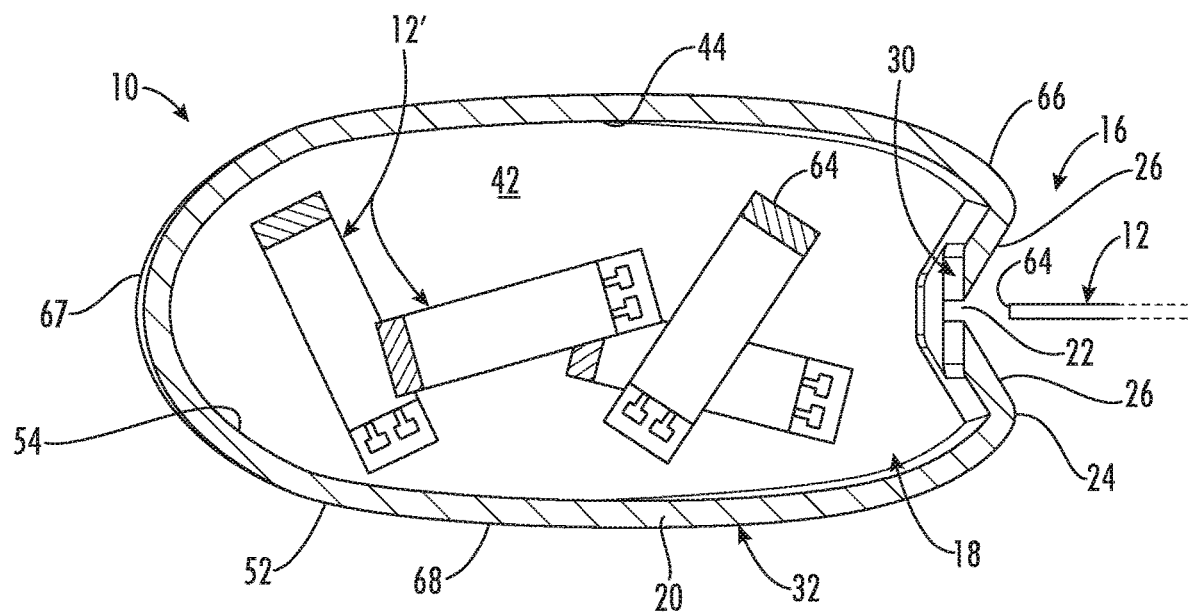
FIG. 3 shows a top view of the embodiment of the container of FIG. 2.
Figure 4:
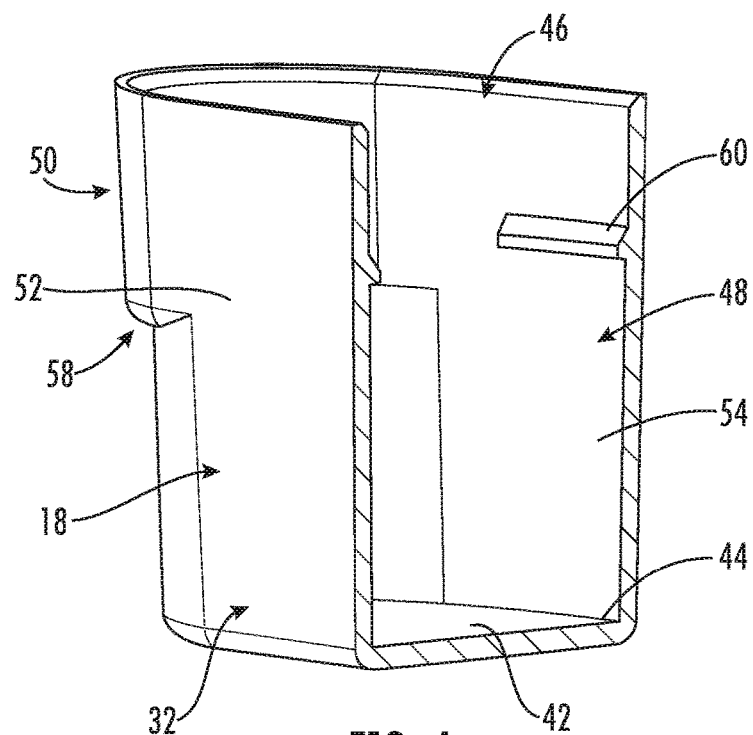
FIG. 4 shows a cutaway perspective view of the embodiment of the container of FIG. 2.
Figure 5:
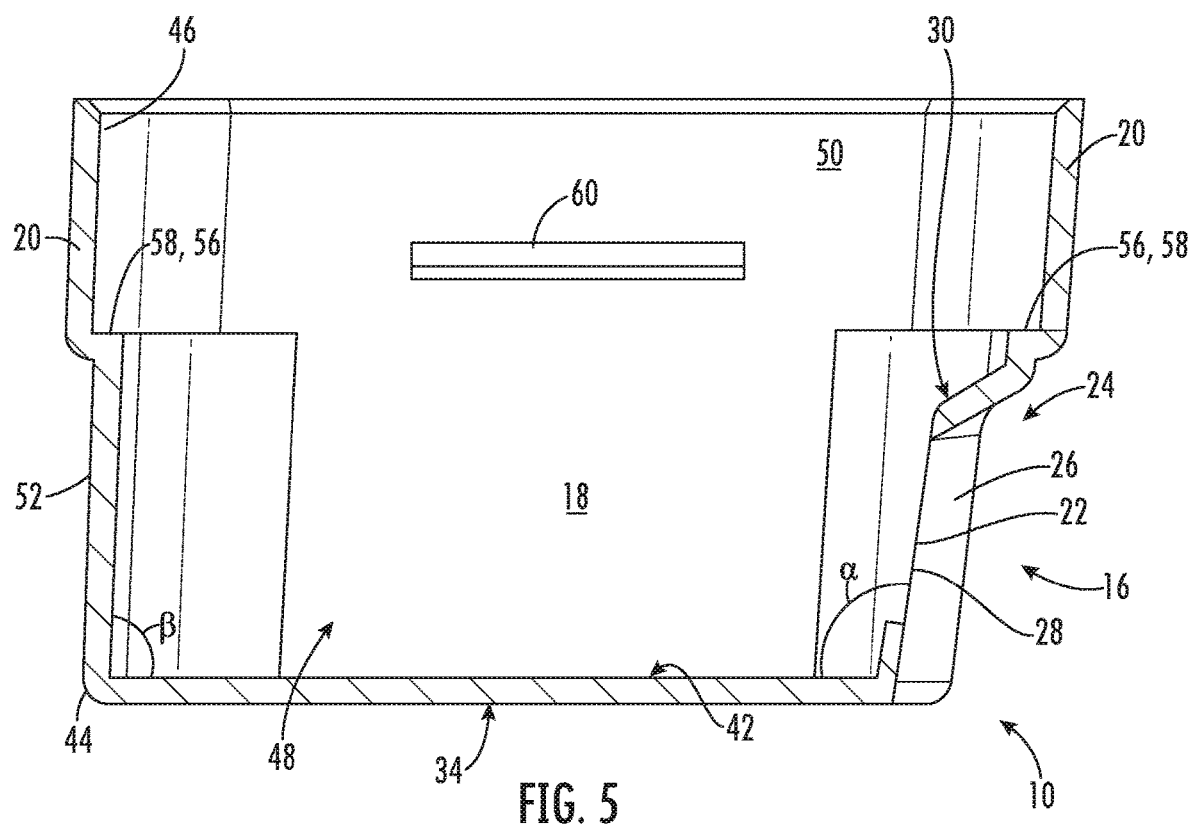
FIG. 5 shows a cross-sectional view of the embodiment of the container of FIG. 2.
Figure 6:
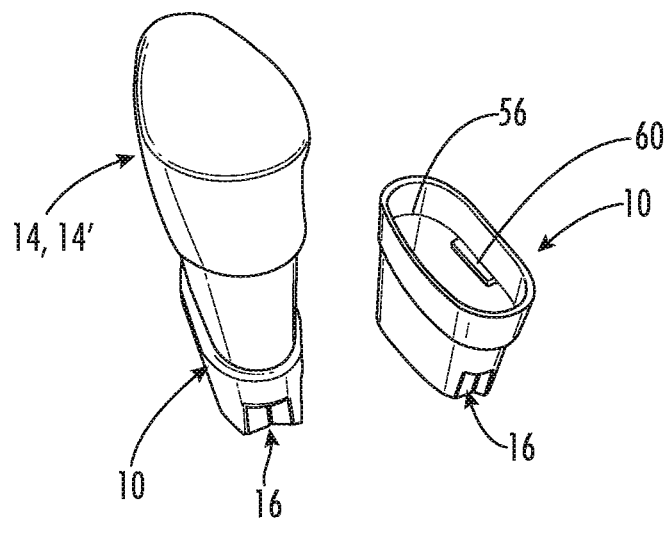
FIG. 6 shows a side-by-side perspective view of the container of FIG. 1 in a use-condition and separately from a use-condition.

Within the interior space 48, the sidewall 32 comprises an interior surface 54 having various elements as herein described with regard to particular embodiments. In one such embodiment, as shown in FIGS. 2, 4 and 5, the interior surface 54 is contoured or otherwise provided with at least one ledge 56 spaced downwardly from the top opening 46, which delineates a transition from the engagement portion 50 to the receptacle portion 18. For example, as shown in FIG. 2 or in FIG. 5, at least one ledge 56 comprising a shoulder 58 may be provided where the engagement portion 50 abuts the receptacle portion 18 such that a vial 14 received through the top opening 46 may only proceed to engage the engagement portion 50 up to the shoulder 58, which serves as a stop element when the bottom of the vial reaches the shoulder. Alternatively or in addition, at least one ledge 56 comprises an inwardly extending rib or tab 60. In one aspect, the rib or tab 60 comprises one feature of a snap-fit system for providing a snap-fit engagement with a vial 14 having a corresponding feature provided partially or fully about the bottom periphery of the vial. A person of ordinary skill will come to understand the typical nature of such snap-fit engagement systems, including opposing resiliently deflectable ribs or tabs which are engaged to releasably retain one structure being received within a cavity of another structure.

The interior surface 54 of the sidewall at the insertion portion 16 follows the contour defined by the inwardly tapered opposing surfaces 26, and the result defines an interior deflector 30 that deflects loose articles away from the slit 22. That is, the deflector acts essentially as the opposite of the funneling action resulting from the inwardly tapered opposing surfaces 26 when a flat, strip-shaped article is presented to be deposited into the receptacle portion 18 through the slit 22, and significantly decreases the likelihood of an accidental alignment of a loose article 12' with the slit which might permit free extraction or removal of the article from the receptacle portion.

As shown more clearly in FIG. 5, the insertion portion 16 is selectively located in the sidewall 32, spaced upwardly from the base 42, to enable more secure retention of an article 12' within the receptacle portion 18. Further, as may be more clearly shown in FIGS. 1 and 2, the slit 22 is oriented orthogonally to the base 42. In this orientation, it is even more difficult or unlikely for a loose article 12' such as a flat, strip-shaped biosensor, which most likely will lay in the receptacle portion 18 in a generally horizontal orientation, from re-orienting to a vertical position which would be required for perfect alignment with the slit 22.

In one aspect, the slit 22 is dimensioned in order to receive a narrow end 64 of a long, flat, strip-shaped article 12. This dimension not only requires a very specific alignment of the article for passage of the article through the slit, it also minimizes the area of the opening between the external environment and the interior space 48 of the receptacle portion 18. In other aspects, the dimension of the slit 22 has a length and width corresponding to the length and width of the end 64 of an article intended for deposit into the receptacle portion plus a minimal percentage overage at each of the length and width to sufficiently enable the passage of the article 12. In further aspects, the dimension of the length and width of the slit is no more than 5% to 50% greater than each of the respective length and width dimensions of the article.

As shown in the embodiment of FIGS. 1-6, the insertion portion 16 is located at a front wall 66 of the disposal container 10, wherein 'front' is relative to the particular vial shown in the drawings for purposes of context for such embodiment. It will be understood upon having this disclosure that the insertion portion might also be located in either of the long sides 68 of the non-round container 14', or in a back wall 67 of non-round container 14'. Further, the orientation of the 'front' of the vial is not limiting as to the scope of any claims relating to this embodiment, and indeed a non-round vial 14' may have a lid 70 that hinges either at a long side or on a short side of the non-round vial.

Referring now to FIGS. 7-13, in alternative embodiments of the disposal container 10 the insertion portion 16' is located in a top wall 36 of the disposal container, and the container is configured for mountable engagement with a round flip top vial 14". The manner of engagement by an engagement portion in such embodiments can be varied by design preference.

Figure 7:
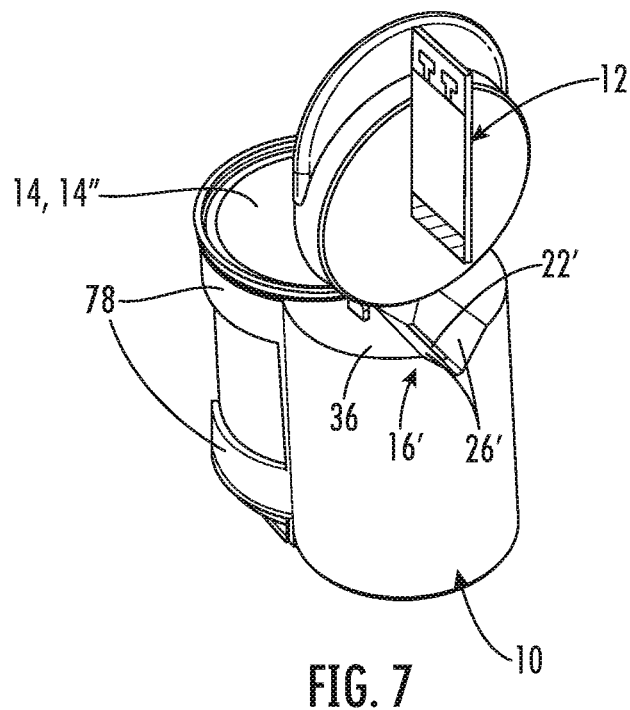
FIG. 7 shows a perspective view of another embodiment of a disposal container in a use-condition mounted to a side of a round flip-top vial.
Figure 12:
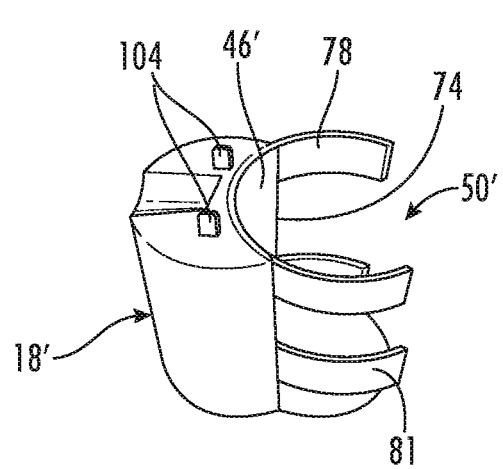
FIG. 12 shows a perspective view of the embodiment of the container shown in FIG. 7.
Figure 13:
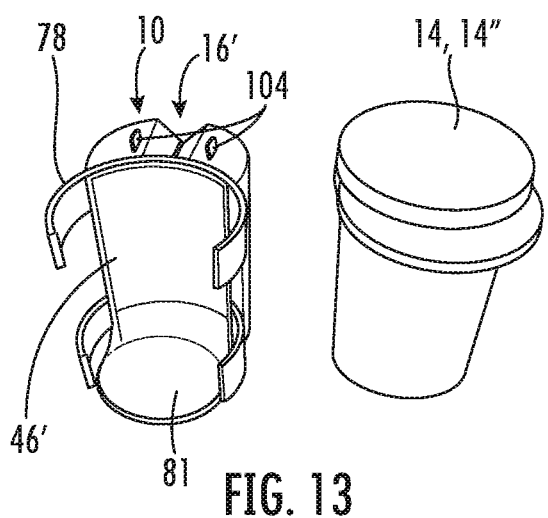
FIG. 13 shows a side-by-side perspective view of the container of FIG. 12 adjacent a round flip top vial to be received by the engagement portion of the container.

In the embodiment shown in FIGS. 7, 12 and 13, the engagement portion 50' and the receptacle portion 18' are side by side, in contrast to the top-to-bottom relation of the embodiment of FIG. 1. In the side by side relation, the engagement portion 50' receives at least a portion of a vertically oriented round flip top vial 14", and is configured accordingly with a concave portion 74 that matches the exterior contour 75 of the round vial 14". As shown in this embodiment, the manner of engagement for achieving the releasable mounting of the container 10 to the vial 14" comprises at least one retention structure 76 for partially or fully encompassing at least a portion of the circumference of the vial 14". In one aspect, the retention structure 76 comprises at least one pair of opposing resiliently deflectable clip arms 78 wherein the vial 14" may engage the container 10 either by laterally forcing the vial between the clip arms 78 or by sliding the vial downwardly into the grip of the clip arms. In another aspect, the retention structure 76 comprises a ring 80 through which the vial 14" is slid. In a typical round flip top vial 14", such as is used to contain. e.g. ACCU-CHEK Aviva blood glucose test strips, a flange 82 located about the top opening 84 of the vial serves as a stop so that the vial 14" does not slide entirely through the ring 80. In yet another aspect, the engagement portion 50' comprises a support platform 81 extending laterally from the base 42' of the receptacle portion 18' for supporting a vial engaged in the retention structure 76 of the engagement portion 50'. In either aspect of clip arms 78 or ring 80 or support platform 81, the radius should be configured to engage a sufficiently tight fit of the vial 14" within the retention structure 76 such that the vial is frictionally secured to achieve robust and stable engagement of the vial with the engagement portion 50'.

In contrast to the embodiment shown in FIG. 1 in which the opening is provided at the top of the container, in one aspect of the embodiment of FIG. 7 and more clearly seen in FIG. 13, the walls 32' of the container 10 define a side opening 46' wherein the interior space 48' of the receptacle portion 18' is open laterally, adjacent the engagement portion 50', such that the receptacle portion 18' is closed to the environment (other than through the slit 22' of the insertion portion 16') only when a vial 14" is engaged with the engagement portion 50'. In this way, as can be seen in FIG. 13, the receptacle portion 18' may be emptied of any contents by disengaging the vial 14" and releasing the contents 12' through the side opening 46'. In this aspect, the concave portion 74 of the container 10 at the engagement portion 50' is closely contoured to match an exterior surface 75 of the vial in order to close off the side opening 46' while in use for storage of used or contaminated articles 12'. Also in this aspect, the arms 78 of retention structure 76 are similarly configured to secure the vial against the side opening.

In other aspects of the embodiment of FIG. 7, the walls 32' of the container fully encompass the interior space 48' of the container except for the access enabled by the presence of the slit 22' in the insertion portion. As such, the container of this aspect is not generally able to be emptied of its contents 12', resulting in disposal of the entire container 10 when full or no longer in use.

Figure 11:
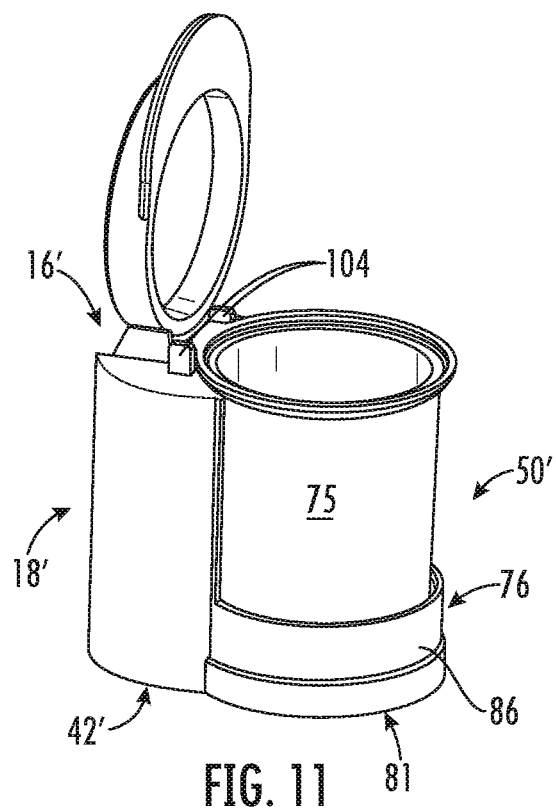
FIG. 11 shows a perspective view of a further alternative of the embodiment of the container of FIG. 8 wherein the bottom of the container is fixed with no bottom hatch.

FIGS. 8-11 show alternative aspects (FIGS. 8-10 and FIG. 11) wherein the retention structure 76 of the engagement portion 50' of the container 10 comprises a cupped support platform 81 that receives a vial 14" and releasably retains it adjacent the receptacle portion 18' in a frictional engagement. The cupped support platform 81 may comprise, for example, an upwardly extending peripheral wall 86 rising from the periphery of a cup bottom. In one aspect, as shown in FIG. 11, the retention structure 76 is a static element of the container 10 and integrally manufactured adjacent the receptacle portion 18'. Similar to the embodiment of FIG. 7, in one aspect the receptacle portion 18' may define a side opening 46' which is closed by engagement of the container 10 with a vial 14" whereby the interior space 48' of the receptacle portion 18' may be emptied when the container is not engaged with a vial, or in another aspect there is no side opening and the walls 20' of the container 10 fully encompass the interior space 48' of the container except for the access enabled by the presence of the slit 22' in the insertion portion 16'. Whether the side opening 46' is provided or not is a design choice depending on the desire to make the container emptiable (for further use) or not (i.e. as a single-use disposable).

Figure 8:
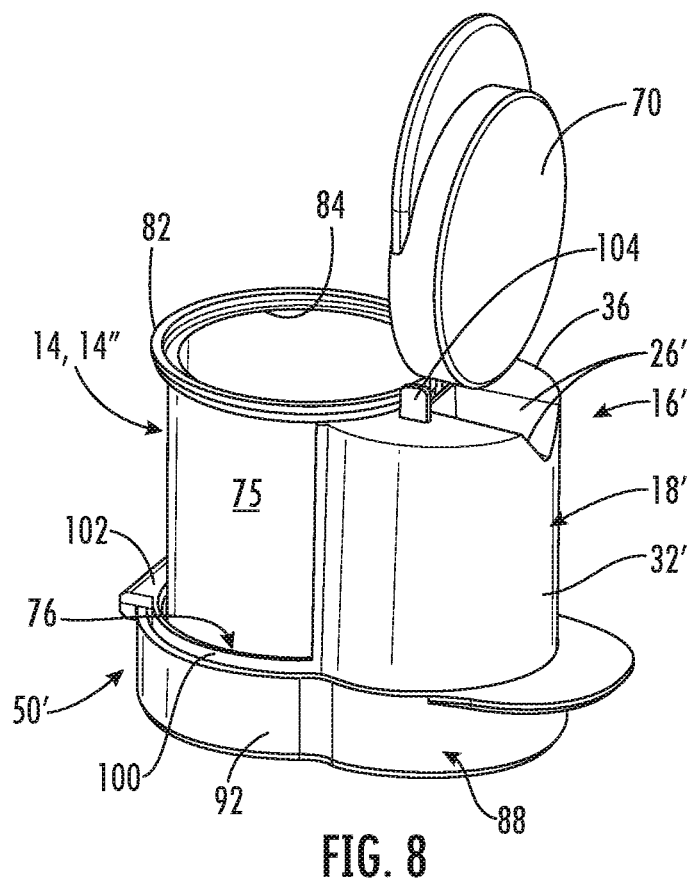
FIG. 8 shows a perspective view of an alternative embodiment of the container of FIG. 7 wherein the container includes a bottom hatch in a closed position.
Figure 9:
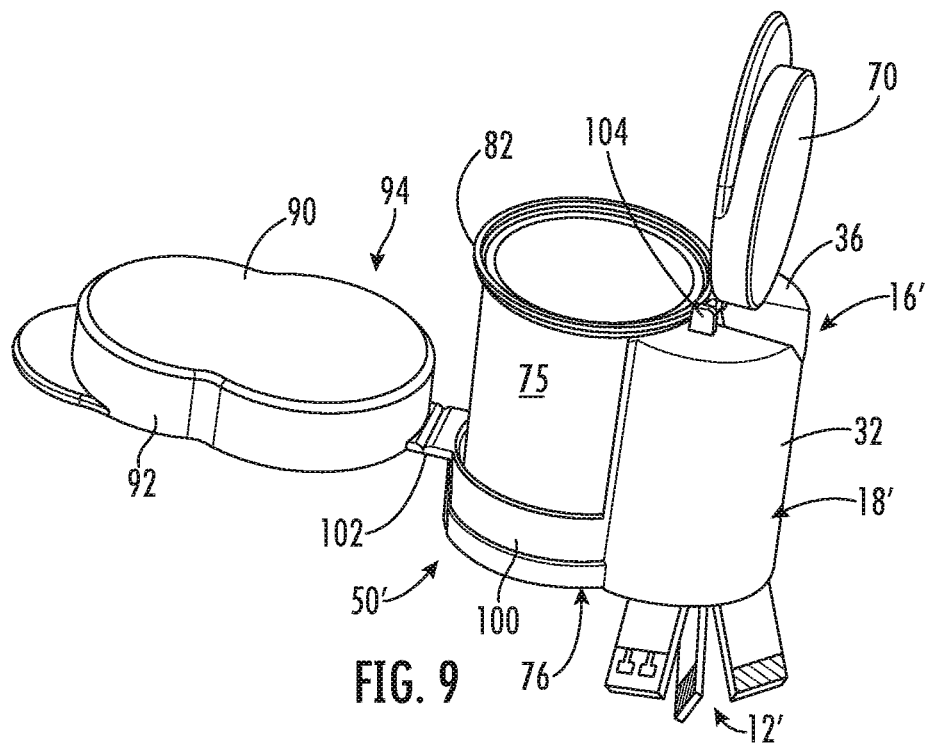
FIG. 9 shows the alternate embodiment of the container of FIG. 8 having the bottom hatch in an open position.
Figure 10:
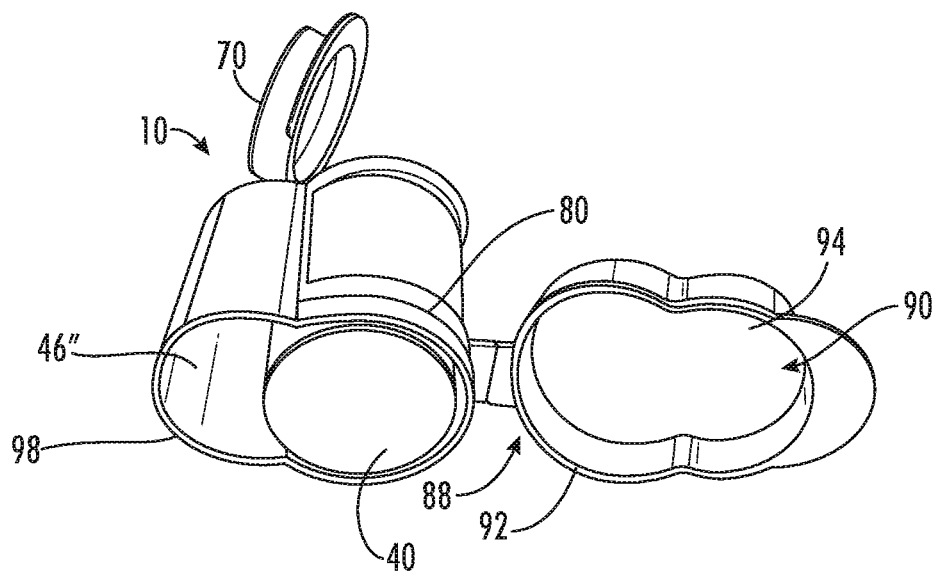
FIG. 10 shows a bottom perspective view of the embodiment of the container of FIGS. 8 and 9 having the bottom hatch separated to show the receptacle portion and the round flip top vial as engaged by the container.

In an alternative aspect more clearly shown in FIG. 8, the retention structure 76 further comprises a hatch 88 operable to close off the interior space 48' of the receptacle portion 18' or to open up a portion of the receptacle portion to enable emptying the contents thereof. In one aspect, the hatch 88 comprises a planar closing surface 90 having a rim 92, wherein the closing surface 90 and the rim 92 cooperate as a cap 94 that frictionally engages a periphery 96 of an opening 46" defined by sidewalls 32' at a lower end 98 of the receptacle portion 18' when the hatch 88 is in a closed position. In another aspect, the hatch 88 also comprises the cupped support platform 81 for the retaining structure 76, wherein the retaining structure further comprises an annular ring 100 configured to receive the lower portion 40' of a vial 14" and the closing surface 90 and rim 92 engage the annular ring 100 when the hatch is in the closed position. The hatch 88 may be hingedly mounted to the annular ring 100, wherein the hatch pivots at a living hinge 102 in order to reposition from the open position to the closed position and vice versa.

As may be more clearly illustrated in FIGS. 7-9 and 11, embodiments of the container 10 having the insertion portion 16' on the top wall 36, the container 10 may include brackets 104 flanking the insertion portion 16' for aligning the container with the hinge of the lid 70, in order to obstruct the insertion portion when the vial lid is in an open position. As previously described, positioning the hinge between brackets 104 maintains the vial 14" in a generally fixed position relative to the container 10. In addition, by aligning the hinge of the vial 14" between the brackets, thereby obstructing the use of the insertion portion 16', the insertion portion becomes relatively isolated from unused biosensors that are provided in the vial, during the time the lid 70 is in an open position.

It will be appreciated in view of this disclosure that the embodiment of FIGS. 7-13 may alternatively be configured for a lateral (side-by-side) engagement of a non-round vial, such as an oval vial. An exemplary oval vial is one which is used to contain, e.g., ACCU-CHEK Guide blood glucose test strips. Whether the disposal container is configured to engage a round or non-round vial is essentially a design choice as to which vial configuration the container is intended to be paired for use. Otherwise, the structural elements should largely remain the same albeit with the possibility of minor and straightforward orientation or contour alterations.

The embodiments of the disposal container of the present invention can be manufactured with any appropriate material for achieving the benefits and advantages of the invention as claimed. In some aspects of the disclosed embodiments, the container is made of a semi-pliable plastic, such as a polycarbonate plastic. In other aspects of the disclosed embodiment, the container is made of a high density flexible plastic. In yet other embodiments, the container is made of a biocidal material such as a semi-pliable biocidal plastic material which provides a risk mitigation in connection with used or otherwise contaminated biosensors deposited into the receptacle portion to prevent or reduce any hygienic concerns with having a receptacle filled with potentially biohazardous biosensors used to analyze bodily fluids such as blood.

For those aspects of the embodiments wherein the container is made of a plastic material, the method of forming the container may be any suitable formation method relating to plastics, such as blow molding, injection molding, and the like. A person of ordinary skill will come to understand, based on the disclosure herein, appropriate methods of manufacture for containers made of plastic materials as well as other methods of manufacture that may be appropriate for embodiments of the container which may be made of, for example, metal or rubber, which may also provide a sufficiently durable material for the container of the present invention to ensure a durable, robust and resilient container.

Figure 15:
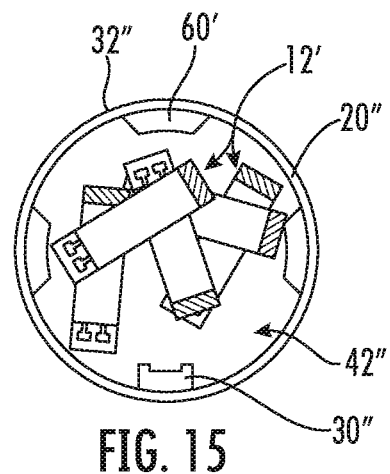
FIG. 15 shows a top view of the embodiment of a disposal container of FIG. 14.
Figure 16:
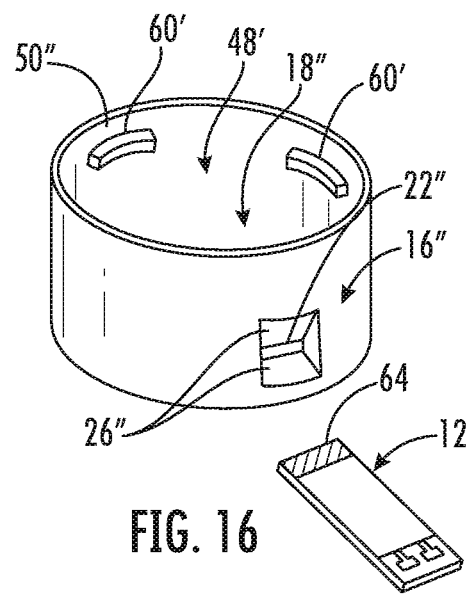
FIG. 16 shows a perspective view of the embodiment of the container of FIG. 14.
Figure 17B:
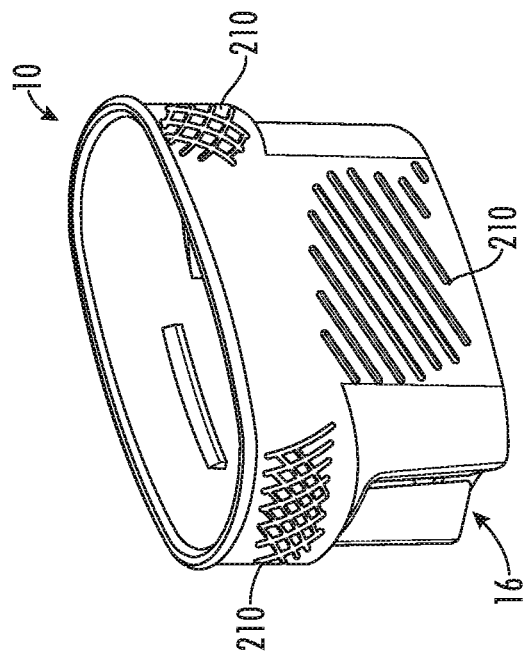
FIG. 17 shows embodiments (a)-(d) of containers comprising integrally formed or surface-coated surface features configured for enhanced gripping of the container by a user.
Figure 17A:
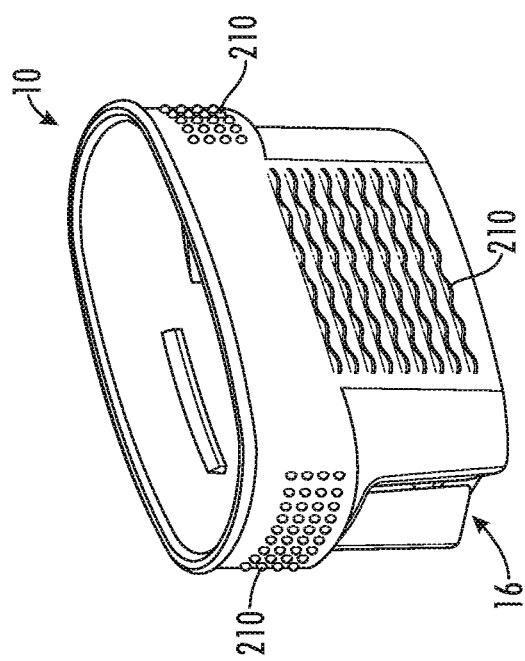
Figure 17D:
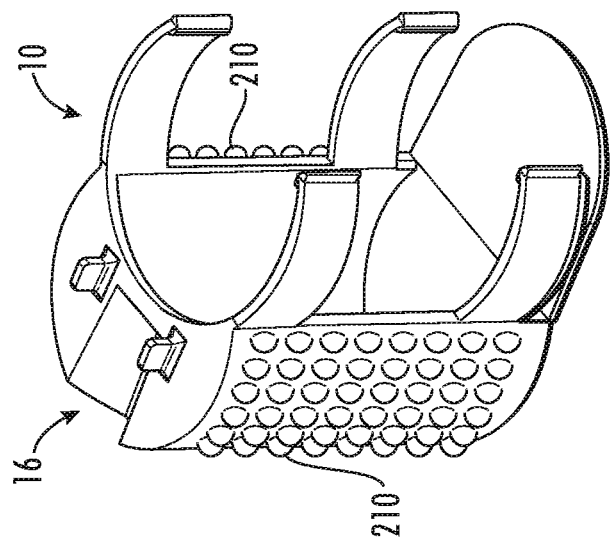
Figure 17C:
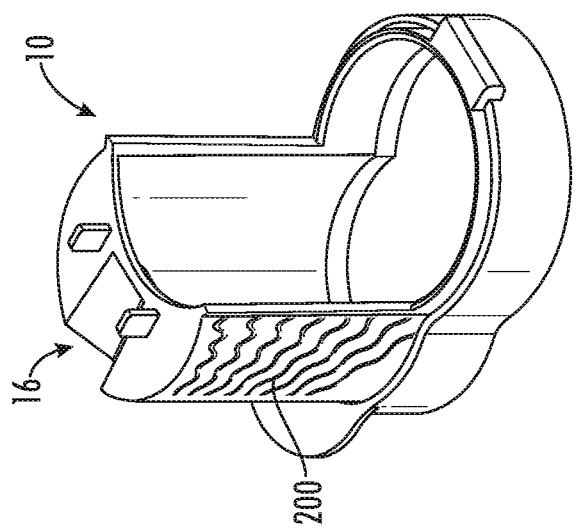

It will be appreciated upon review of this disclosure that the embodiment of FIGS. 1-6 may alternatively be configured for a bottom cap engagement of a round vial 14", such as a flip top vial. Exemplary embodiments of such alternative may be better understood by reference to FIGS. 14-16, wherein like elements are numerically referenced using a single-prime (') or double-prime (") designation, such as 14", 16", 18", etc. An exemplary round flip top vial is one which is used to contain, e.g., ACCU-CHEK Aviva blood glucose test strips. Whether the disposal container 10 is configured to engage a round 14" or non-round 14' vial is essentially a design choice as to which vial configuration the container is intended to be paired for use. Otherwise, the structural elements should largely remain the same albeit with the possibility of minor and straightforward orientation or contour alterations.

In any of the embodiments disclosed herein, a non-slip or other grip enhancing coating or surface feature may be provided as desired on the exterior 52 of sidewall 32 or portions thereof. FIG. 17 illustrates exemplary embodiments (a) through (d) wherein the exterior surface 52, 52' is either integrally formed with areas having surface features or contours 200 that provide a tactile grip when handled manually by a user; or alternatively coated in one or more areas with a separate material 210, such as non-slip rubber. Features/contours 200 and material 210 may be in the form of raised dots, depressed dimples, raised or depressed waves, raised or depressed scales, cross-hatching, or any other form which provides a natural tactile grip for users.

One advantage of the present invention previously noted as an area for improvement regarding biosensor disposal practices is that the reusable nature of the disclosed container avoids separate self-contained and disposable (i.e. single-use) disposal containers from adding to the volume of discarded articles for trash or landfill collection, wherein having a container that retains biosensors while in use but can be emptied for further use not only saves waste from the container itself but also reduces the resources that would otherwise be required for manufacture of single-use containers that are always discarded when filled. However, whereas previous embodiments have been designed with the ability for a user to dispose of used test strips and "reuse" the container, according to an alternative embodiment a boundary wall divides the receptacle portion from the engagement portion of the container in order to provide a completely closed receptacle portion. In such embodiments, the engagement portion is still configured to detachably receive a vial, but once the receptacle portion is filled with used biosensors, the container is discarded. However, in order to achieve a similar advantage, a usage protocol is provided wherein the container may be sent by the user to a medical waste management and/or recycling center. For purposes of further clarification, the receptacle portion is completely closed on all sides except for the slit where the used biosensor insertion is possible. Alternatively, the boundary wall may be configured for closure of the receptacle portion after one or more times of filling the receptacle with used biosensors. In such embodiments, shipping of "contaminated" (or used) biosensors to a medical waste management and/or recycling center can be arranged, such as according to a protocol in which, e.g., a vendor supplies specially detailed mail pouches for shipping of used strips through a mail carrier system.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

The present invention disclosed herein comprises, among other aspects, the embodiments of non-ornamental structural elements as described in this specification and correspondingly shown in (a) FIGS. 1-6; (b) FIGS. 7, 12 and 13; (c) FIGS. 8-10; (d) FIG. 11; (e) FIGS. 14-16; and (f) FIG. 17. Such embodiments include:

I. A container comprising a generally planar base having a periphery; a sidewall extending upwardly from the periphery of the base to a top opening, the base and sidewall defining an interior space having a receptacle portion and an engagement portion, the receptacle portion located proximal to the base and configured for receiving and retaining a plurality of flat strip-shaped articles, and the engagement portion located distally to the base and configured to detachably receive and retain a lower portion of a vial via a fitted engagement proximate to the top opening; the sidewall having an insertion portion comprising a slit configured to receive a single flat strip-shaped article into the receptacle portion, the insertion portion further comprising a pair of generally planar and rigid opposing surfaces tapered inwardly from an exterior of the sidewall to the slit, the slit being generally defined in the area where the tapered opposing surfaces converge, the tapered opposing surfaces being configured to facilitate alignment of a flat strip-shaped article for insertion through the slit into the receptacle portion; the sidewall further comprising an interior surface, wherein the interior surface in the engagement portion is contoured to define at least one ledge spaced downwardly from the top opening and delineating a transition from the engagement portion to the receptacle portion, wherein the at least one ledge comprises a stop configured to prevent the portion of a vial received in the engagement portion from extending into the receptacle portion; and wherein the interior surface at the insertion portion is contoured in accordance with the inwardly tapered opposing surfaces to define an interior deflector configured to deflect any loose flat strip-shaped articles contained within the receptacle portion from accidental alignment with the slit which would cause free extraction of said article.

II. A container configured for mountable engagement with a round vial, comprising a receptacle portion and an engagement portion, the receptacle portion comprising a generally upstanding cylinder having a base, an upstanding wall, and a top wall having an insertion portion comprising a slit configured to receive a single flat strip-shaped article into the receptacle portion, the insertion portion further comprising a pair of generally planar and rigid opposing surfaces tapered inwardly from an exterior of the sidewall to the slit, the slit being generally defined in the area where the tapered opposing surfaces converge, the tapered opposing surfaces being configured to facilitate alignment of a flat strip-shaped article for insertion through the slit into the receptacle portion, the interior surface at the insertion portion being contoured in accordance with the inwardly tapered opposing surfaces to define an interior deflector configured to deflect any loose flat strip-shaped articles contained within the receptacle portion from accidental alignment with the slit which would cause free extraction of said article, the engagement portion comprising an opening at one side of the receptacle portion configured to receive at least a portion of a vertically oriented round vial, the opening comprising a concave portion that matches the exterior contour of said round vial, the engagement portion further comprising a retention structure having at least one pair of opposing resiliently deflectable clip arms configured for receiving the round vial either laterally or vertically, and a support platform extending laterally from a base of the receptacle portion configured for supporting a vial engaged in the retention structure.

III. A container configured for mountable engagement with a round vial, comprising a receptacle portion and an engagement portion, the receptacle portion comprising a generally upstanding cylinder having a base, an upstanding wall, and a top wall having an insertion portion comprising a slit configured to receive a single flat strip-shaped article into the receptacle portion, the insertion portion further comprising a pair of generally planar and rigid opposing surfaces tapered inwardly from an exterior of the sidewall to the slit, the slit being generally defined in the area where the tapered opposing surfaces converge, the tapered opposing surfaces being configured to facilitate alignment of a flat strip-shaped article for insertion through the slit into the receptacle portion, the interior surface at the insertion portion being contoured in accordance with the inwardly tapered opposing surfaces to define an interior deflector configured to deflect any loose flat strip-shaped articles contained within the receptacle portion from accidental alignment with the slit which would cause free extraction of said article, the engagement portion comprising an opening at one side of the receptacle portion configured to receive at least a portion of a vertically oriented round vial, the opening comprising a concave portion that matches the exterior contour of said round vial, the engagement portion further comprising a retention structure comprising a cupped support platform extending laterally from a base of the receptacle portion configured for supporting and retaining a vial engaged in the retention structure, the base and the cupped support platform including a hatch hingedly connected at one side of the periphery of the base which operates to open or close the receptacle portion at the base, and to provide the cup bottom to support the vial when in a closed position.

IV. A container configured for mountable engagement with a round vial, comprising a receptacle portion and an engagement portion, the receptacle portion comprising a generally upstanding cylinder having a base, an upstanding wall, and a top wall having an insertion portion comprising a slit configured to receive a single flat strip-shaped article into the receptacle portion, the insertion portion further comprising a pair of generally planar and rigid opposing surfaces tapered inwardly from an exterior of the sidewall to the slit, the slit being generally defined in the area where the tapered opposing surfaces converge, the tapered opposing surfaces being configured to facilitate alignment of a flat strip-shaped article for insertion through the slit into the receptacle portion, the interior surface at the insertion portion being contoured in accordance with the inwardly tapered opposing surfaces to define an interior deflector configured to deflect any loose flat strip-shaped articles contained within the receptacle portion from accidental alignment with the slit which would cause free extraction of said article, the engagement portion comprising an opening at one side of the receptacle portion configured to receive at least a portion of a vertically oriented round vial, the opening comprising a concave portion that matches the exterior contour of said round vial, the engagement portion further comprising a retention structure comprising a cupped support platform extending laterally from a base of the receptacle portion configured for supporting and retaining a vial engaged in the retention structure.

Figure 14:
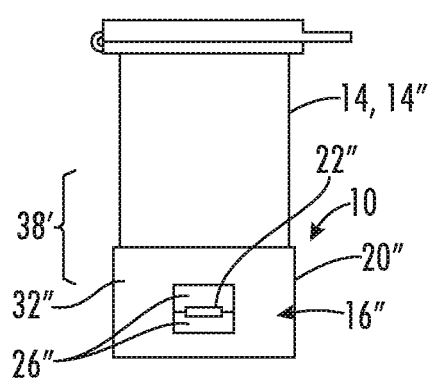
FIG. 14 shows a side elevation view of another embodiment of a disposal container in a use-condition mounted in a bottom cap style to a round flip-top vial.

V. The container described in I., wherein the container is configured for mountable attachment to a vial having a non-round configuration such as is shown in FIG. 1, or to a vial having a round configuration such as is shown in FIG. 14.

VI. The container described in any of I, through V., wherein at least a portion of the exterior of the sidewall comprises a non-slip surface feature configured to provide a tactile grip for a user. The surface feature may comprise integrally formed surface features in the exterior sidewall, and/or may comprise features formed by a surface material applied to the exterior of the sidewall.

VII. The container described in any of I, through VI., wherein at least a portion of the upstanding wall or upwardly extending sidewall comprises a transparent or translucent window enabling visualization of the interior space of the receptacle portion. Alternatively, the container at least about the receptacle portion, is comprised of a transparent or translucent material such that the majority if not entirety of the interior space of the receptacle portion can be seen by a user. In such embodiments, a user of the container is able to visually inspect and discern the level of fill of the receptacle portion with used biosensors in order to determine whether a need exists to empty the receptacle portion for further use.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A container comprising:
   a generally planar base having a periphery;
   a sidewall extending upwardly from the periphery of the base to a top opening;
   the base and sidewall defining an interior space having a receptacle portion and an engagement portion;
   the receptacle portion located proximal to the base and configured for receiving and retaining a plurality of flat strip-shaped articles,
   the engagement portion located distally to the base and configured to detachably receive and retain a lower portion of a vial via a fitted engagement proximate to the top opening;
   the sidewall having an insertion portion comprising a slit configured to receive a single flat strip-shaped article into the receptacle portion, the insertion portion further comprising a pair of generally planar and rigid opposing surfaces tapered inwardly from an exterior of the sidewall to the slit, the slit being generally defined in the area where the tapered opposing surfaces converge, the tapered opposing surfaces being configured to facilitate alignment of a flat strip-shaped article for insertion through the slit into the receptacle portion;
   the sidewall further comprising an interior surface, wherein the interior surface in the engagement portion is contoured to define at least one ledge spaced downwardly from the top opening and delineating a transition from the engagement portion to the receptacle portion, wherein the at least one ledge comprises a stop configured to prevent the portion of a vial received in the engagement portion from extending into the receptacle portion;

and wherein the interior surface at the insertion portion is contoured in accordance with the inwardly tapered opposing surfaces to define an interior deflector configured to deflect any loose flat strip-shaped articles contained within the receptacle portion from accidental alignment with the slit which would cause free extraction of said article.

2. The container of claim 1, wherein the fitted engagement proximate the top opening comprises a snap-fit system provided on the interior surface of the sidewall in the engagement portion.

3. The container of claim 2, wherein the snap-fit system comprises a plurality of inwardly extending tabs on the interior surface of the sidewall in the engagement portion, the tabs being spaced apart downwardly from the top opening and configured to frictionally engage a corresponding ridge provided on a lower portion of a vial inserted into the engagement portion.

4. The container of claim 1, wherein the fitted engagement comprises a frictional retention arrangement wherein the top opening and an interior surface of the engagement portion are shaped according to the exterior dimensions of a lower portion of a vial to be inserted therein.

5. The container of claim 1, wherein the slit has a generally vertical orientation and the insertion portion is located in the sidewall at a location spaced upwardly from the base.

6. The container of claim 1, wherein the slit has a length and width dimensioned to just accommodate the length and width of a flat strip-shaped article intended for insertion therethrough.

7. The container of claim 6, wherein the length and width dimensions of the slit are no more than 50% larger than the length and width of a flat strip-shaped article intended for insertion therethrough, whereby the likelihood of accidental alignment of a loose article within the receptacle portion is minimized.

8. The container of claim 1, wherein the base has a non-round shape.

9. The container of claim 8, wherein the base comprises a generally oval shape and the sidewall in coordination with the base comprises a generally oval-shaped cylinder having opposing first and second short ends, the insertion portion being located in the sidewall at one of the first and second short ends.

10. The container of claim 9, wherein the sidewall extends upwardly from the base non-vertically such that an interior angle $\beta$ between the base and the sidewall at the first short end is generally acute, and an interior angle □ between the base and the sidewall at the second short end is generally obtuse.

11. The container of claim 10, wherein the interior angle □ is greater than 90 degrees and less than about 120 degrees, and the interior angle $\beta$ is greater than about 60 degrees and less than 90 degrees.

12. The container of claim 1, wherein the at least one ledge comprises a generally planar surface extending entirely within the interior space and completely dividing the receptacle portion from the engagement portion such that the only access into the receptacle portion is through the slit.

13. The container of claim 1, wherein at least a portion of the exterior of the sidewall comprises a non-slip surface feature configured to provide a tactile grip for a user.

14. The container of claim 13, wherein the surface feature comprises at least one of a contour integrally formed into the exterior of the sidewall, and a material applied to the exterior of the sidewall.

15. The container of claim 14, wherein the surface feature comprises at least one of raised dots, depressed dimples, raised wavy lines, depressed wavy lines, raised scales, depressed scales, and cross-hatching.

* * * * *